United States Patent

Leven

(10) Patent No.: US 11,172,959 B2
(45) Date of Patent: Nov. 16, 2021

(54) LONG, FLEXIBLE SHEATH AND LEAD BLANK AND SYSTEMS AND METHODS OF MAKING AND USING

(71) Applicant: Boston Scientific Neuromodulation Corporation, Valencia, CA (US)

(72) Inventor: Jacob B. Leven, Huntington Beach, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 226 days.

(21) Appl. No.: 16/399,779

(22) Filed: Apr. 30, 2019

(65) Prior Publication Data

US 2019/0336165 A1 Nov. 7, 2019

Related U.S. Application Data

(60) Provisional application No. 62/665,732, filed on May 2, 2018.

(51) Int. Cl.
*A61B 17/34* (2006.01)
*A61N 1/05* (2006.01)

(52) U.S. Cl.
CPC ...... *A61B 17/3468* (2013.01); *A61B 17/3401* (2013.01); *A61N 1/0558* (2013.01)

(58) Field of Classification Search
CPC ...... A61N 1/05; A61N 1/0551; A61N 1/0553; A61N 1/0556; A61B 17/3468
See application file for complete search history.

(56) References Cited

U.S. PATENT DOCUMENTS

| | | | |
|---|---|---|---|
| 4,602,624 A | 7/1986 | Naples et al. |
| 4,630,611 A | 12/1986 | King |
| 4,744,370 A | 5/1988 | Harris |
| 5,000,194 A | 3/1991 | van den Honert et al. |
| 5,070,605 A | 12/1991 | Daglow et al. |
| 5,135,001 A | 8/1992 | Sinofsky et al. |
| 5,300,106 A | 4/1994 | Dahl et al. |
| 5,348,481 A | 9/1994 | Ortiz |
| 5,374,285 A | 12/1994 | Vaiani et al. |
| 5,409,469 A | 4/1995 | Schaerf |
| 5,458,629 A | 10/1995 | Baudino et al. |
| 5,522,874 A | 6/1996 | Gates |

(Continued)

FOREIGN PATENT DOCUMENTS

| | | |
|---|---|---|
| EP | 0580928 A1 | 2/1994 |
| EP | 0650694 B1 | 7/1998 |

(Continued)

*Primary Examiner* — Tuan V Nguyen
(74) *Attorney, Agent, or Firm* — Branch Partners PLLC; Bruce E. Black

(57) ABSTRACT

A method for implanting a lead includes inserting a needle into the patient; inserting a lead blank through the needle; steering the lead blank to, or near, a lead implantation site; removing the needle from the patient and leaving the lead blank; advancing a flexible sheath over the lead blank after removing the needle; removing the lead blank from the patient and leaving the flexible sheath; inserting a lead through the flexible sheath, after removing the lead blank, and implanting the lead at the lead implantation site; and removing the flexible sheath. The flexible sheath can also be used for explanting a lead and, optionally, implanting a new lead.

20 Claims, 10 Drawing Sheets

(56) References Cited

U.S. PATENT DOCUMENTS

| | | |
|---|---|---|
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,987,361 A | 11/1999 | Mortimer |
| 6,018,684 A | 1/2000 | Bartig et al. |
| 6,125,302 A | 9/2000 | Kuzma |
| 6,134,478 A | 10/2000 | Spehr |
| 6,161,047 A | 12/2000 | King et al. |
| 6,162,101 A | 12/2000 | Fischer et al. |
| 6,167,311 A | 12/2000 | Rezai |
| 6,181,969 B1 | 1/2001 | Gord |
| 6,322,559 B1 | 11/2001 | Daulton et al. |
| 6,428,336 B1 | 8/2002 | Akerfeldt |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,609,029 B1 | 8/2003 | Mann et al. |
| 6,609,032 B1 | 8/2003 | Woods et al. |
| 6,663,570 B2 | 12/2003 | Mott et al. |
| 6,678,564 B2 | 1/2004 | Ketterl et al. |
| 6,741,892 B1 | 5/2004 | Meadows et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,108,549 B2 | 9/2006 | Lyu et al. |
| 7,203,548 B2 | 4/2007 | Whitehurst et al. |
| 7,241,180 B1 | 7/2007 | Rentas |
| 7,244,150 B1 | 7/2007 | Brase et al. |
| 7,292,890 B2 | 11/2007 | Whitehurst et al. |
| 7,402,083 B2 | 7/2008 | Kast et al. |
| 7,437,193 B2 | 10/2008 | Parramon et al. |
| 7,450,997 B1 | 11/2008 | Pianca et al. |
| 7,489,971 B1 | 2/2009 | Franz |
| 7,668,601 B2 | 2/2010 | Hegland et al. |
| 7,672,734 B2 | 3/2010 | Anderson et al. |
| 7,736,191 B1 | 6/2010 | Sochor |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 7,993,305 B2 | 8/2011 | Ye et al. |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,074 B2 | 10/2011 | Barker |
| 8,099,177 B2 | 1/2012 | Dahlberg |
| 8,100,726 B2 | 1/2012 | Harlan et al. |
| 8,140,163 B1 | 3/2012 | Daglow et al. |
| 8,175,710 B2 | 5/2012 | He |
| 8,190,259 B1 | 5/2012 | Smith |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,583,237 B2 | 11/2013 | Bedenbaugh |
| 8,688,235 B1 | 4/2014 | Pianca et al. |
| 8,753,313 B2 | 6/2014 | Kimmel et al. |
| 8,849,415 B2 | 9/2014 | Bedenbaugh |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,220,524 B2 | 12/2015 | Boling et al. |
| 9,270,070 B2 | 2/2016 | Pianca |
| 9,289,596 B2 | 3/2016 | Leven |
| 9,352,147 B2 | 5/2016 | Nguyen-stella |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,620 B2 | 11/2016 | Romero et al. |
| 9,504,839 B2 | 11/2016 | Leven |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2005/0015130 A1 | 1/2005 | Gill |
| 2005/0038489 A1 | 2/2005 | Grill |
| 2005/0171587 A1 | 8/2005 | Daglow et al. |
| 2005/0288758 A1* | 12/2005 | Jones ................ A61B 17/3415 607/116 |
| 2006/0025841 A1 | 2/2006 | McIntyre |
| 2006/0247697 A1 | 11/2006 | Sharma et al. |
| 2007/0150036 A1 | 6/2007 | Anderson |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0132933 A1* | 6/2008 | Gerber ................ A61N 1/0534 606/191 |
| 2008/0215125 A1 | 9/2008 | Farah et al. |
| 2008/0255647 A1 | 10/2008 | Jensen et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0276021 A1 | 11/2009 | Meadows et al. |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203302 A1 | 8/2012 | Moffit et al. |

(56) References Cited

U.S. PATENT DOCUMENTS

| | | |
|---|---|---|
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0209285 A1 | 8/2012 | Barker et al. |
| 2012/0232603 A1 | 9/2012 | Sage |
| 2012/0259386 A1 | 10/2012 | DeRohan et al. |
| 2012/0316615 A1 | 12/2012 | DiGiore et al. |
| 2013/0105071 A1 | 5/2013 | DiGiore et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018838 A1 | 1/2015 | Nabutovsky et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0228692 A1 | 8/2016 | Steinke et al. |
| 2016/0296745 A1 | 10/2016 | Govea et al. |
| 2016/0317800 A1* | 11/2016 | Barker .................. A61N 1/05 |
| 2018/0008311 A1* | 1/2018 | Shiroff ................ A61N 1/0551 |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

* cited by examiner

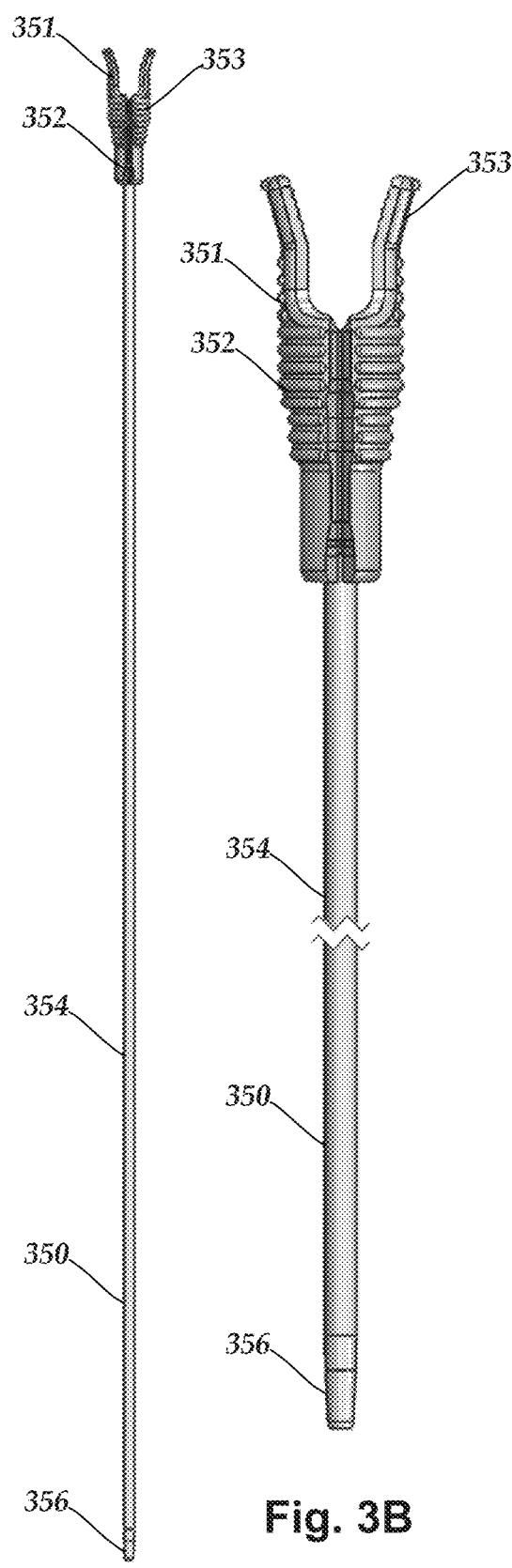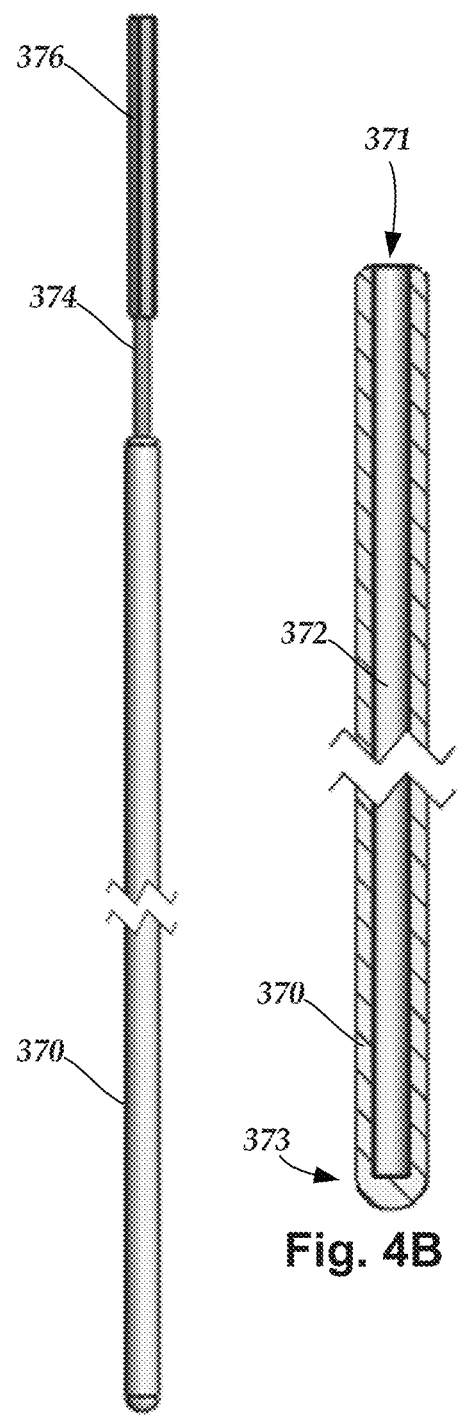
Fig. 3A  Fig. 3B  Fig. 4A  Fig. 4B

LONG, FLEXIBLE SHEATH AND LEAD BLANK AND SYSTEMS AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/665,732, filed May 2, 2018, which is incorporated herein by reference.

FIELD

The present disclosure is directed to the area of implantable electrical stimulation systems and methods of making and using the systems. The present disclosure is also directed to a long, flexible sheath and lead blank for facilitating implantation or explanation of leads into patients, as well as systems containing the sheath and lead blank methods of making and using the sheath and lead blank and leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a sheath for implanting a lead. The sheath includes a flexible body having a proximal end and a distal end and having a length of at least 30 centimeters, the flexible body defining a lumen extending from the flexible end to the distal end, and a rigid hub coupled to the proximal end of the flexible body and defining an opening to the lumen of the flexible body.

In at least some aspects, the rigid hub includes two pull-apart tabs and the flexible body is splittable along a length of the flexible body when the two pull-apart tabs are pulled away from each other. In at least some aspects, the flexible body of the sheath is perforated or scored along the length of the flexible body. In at least some aspects, the sheath has a tapered distal end to reduce an inner diameter of the sheath. In at least some aspects, the sheath is configured to extend into an epidural space of a patient at a lumbar or thoracic vertebral level and extend along the epidural space to a lead implantation site at a cervical vertebral level.

Another aspect is a kit that includes any of the sheaths described above and a lead blank configured for advancement of the sheath over the lead blank and having a length at least as long as the length of the sheath.

In at least some aspects, the lead blank defines a lumen and includes a stylet configured to be disposed in the lumen. In at least some aspects, the stylet is removable from the lumen of the lead blank. In at least some aspects, the stylet is permanently disposed within the lumen of the lead blank.

In at least some aspects, the kit further includes a needle configured and arranged for insertion of the lead blank through the needle. In at least some aspects, the needle has a length that is no more than 40% of the length of the lead blank. In at least some aspects, the kit further includes a lead configured for insertion through the flexible sheath. In at least some aspects, the lead blank is configured to extend into an epidural space of a patient at a lumbar or thoracic vertebral level and extend along the epidural space to a lead implantation site at a cervical vertebral level.

In at least some aspects that lead blank comprises a handle or a suture to facilitate holding the lead blank in place when inserting the sheath over the lead blank.

Yet another aspect is a kit for replacing a first lead. The kit includes any of the sheaths described above and a second lead configured for insertion through the sheath. In at least some aspects, the kit further includes a lead blank configured for insertion through the sheath and having a length at least as long as the length of the sheath.

A further aspect is a method for implanting a lead. The method includes inserting a needle into the patient; inserting a lead blank through the needle; steering the lead blank to, or near, a lead implantation site; removing the needle from the patient and leaving the lead blank; advancing a flexible sheath over the lead blank after removing the needle; removing the lead blank from the patient and leaving the flexible sheath; inserting a lead through the flexible sheath, after removing the lead blank, and implanting the lead at the lead implantation site; and removing the flexible sheath.

In at least some aspects, inserting the needle into the patient includes inserting the needle into an epidural space of the patient at a lumbar or thoracic vertebral level. In at least some aspects, the lead implantation site is at a cervical vertebral level. In at least some aspects, the flexible sheath has a length of at least 30 cm. In at least some aspects, the needle has a length that is no more than 40% of a length of the lead blank In at least some aspects, the steering of the lead blank occurs prior to removal of the needle. In at least some aspects, the flexible sheath includes a flexible body and a rigid hub coupled to the flexible body and including two pull-apart tabs, wherein removing the sheath includes pulling apart the two pull-apart tabs and splitting the flexible body of the sheath. In at least some aspects, steering the lead blank occurs prior to advancing the flexible sheath over the lead blank.

Another aspect is a method for replacing a lead. The method includes advancing a flexible sheath over a first lead implanted in a patient; removing the first lead from the patient and leaving the flexible sheath; inserting a second lead through the flexible sheath, after removing the first lead, and implanting the second lead at a lead implantation site; and removing the flexible sheath.

In at least some aspects, the flexible sheath has a length of at least 30 cm. In at least some aspects, the first lead extends from an epidural space of the patient at a lumbar or thoracic vertebral level to the lead implantation site at a cervical vertebral level.

In at least some aspects, the method further includes inserting a lead blank through the flexible sheath after removing the first lead and prior to inserting the second lead; steering the lead blank to, or near, the lead implantation site;

and removing the lead blank from the patient and leaving the flexible sheath, wherein the second lead is inserted into the flexible sheath after removing the lead blank.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3A is a schematic side view of one embodiment of a long, flexible sheath;

FIG. 3B is a close-up side view of portions of the long, flexible sheath of FIG. 3A;

FIG. 4A is a schematic side view of one embodiment of a lead blank;

FIG. 4B is a close-up cross-sectional view of portions of the lead blank of FIG. 4A;

DETAILED DESCRIPTION

The present disclosure is directed to the area of implantable electrical stimulation systems and methods of making and using the systems. The present disclosure is also directed to a long, flexible sheath and lead blank for facilitating implantation or explanation of leads into patients, as well as systems containing the sheath and lead blank methods of making and using the sheath and lead blank and leads.

The long, flexible sheath and lead blank described herein can be used with electrical stimulation systems, optical stimulation systems, and other implantable leads. Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

A percutaneous lead for electrical stimulation (for example, spinal cord stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes.

Figure 1:
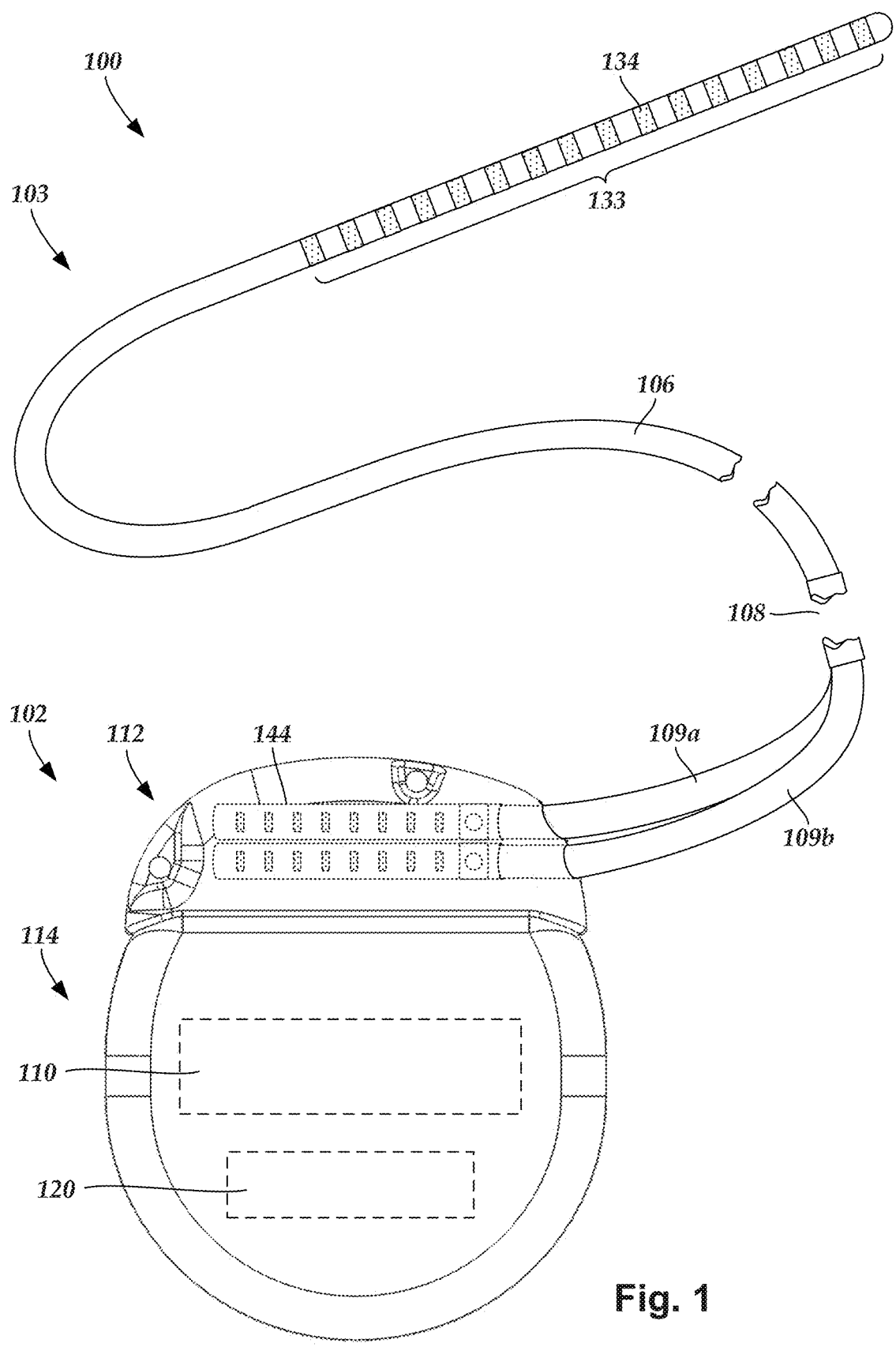
FIG. 1 is a schematic view of one embodiment of an electrical stimulation system.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array 133 of electrodes 134 and an array of terminals (e.g., 210 in FIG. 2A-2B) disposed along the one or more lead bodies 106. In at least some embodiments, the lead is isodiametric along a longitudinal length of the lead body 106. In FIG. 1, the electrical stimulation system 100 is shown having a junction 108 configured to couple to distal portion of the lead 103 to one or more proximal portions 109a and 109b.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
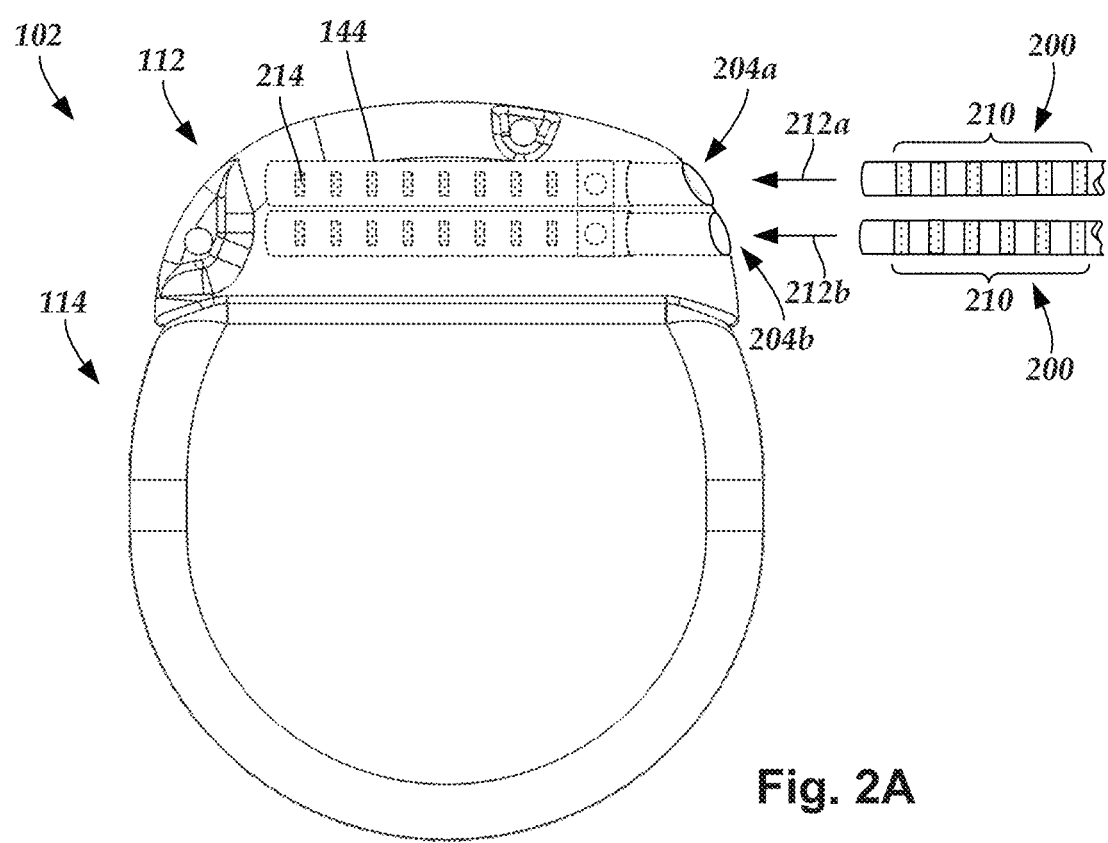
FIG. 2A is a schematic view of one embodiment of a proximal portion of a lead and a control module of an electrical stimulation system.
Figure 2B:
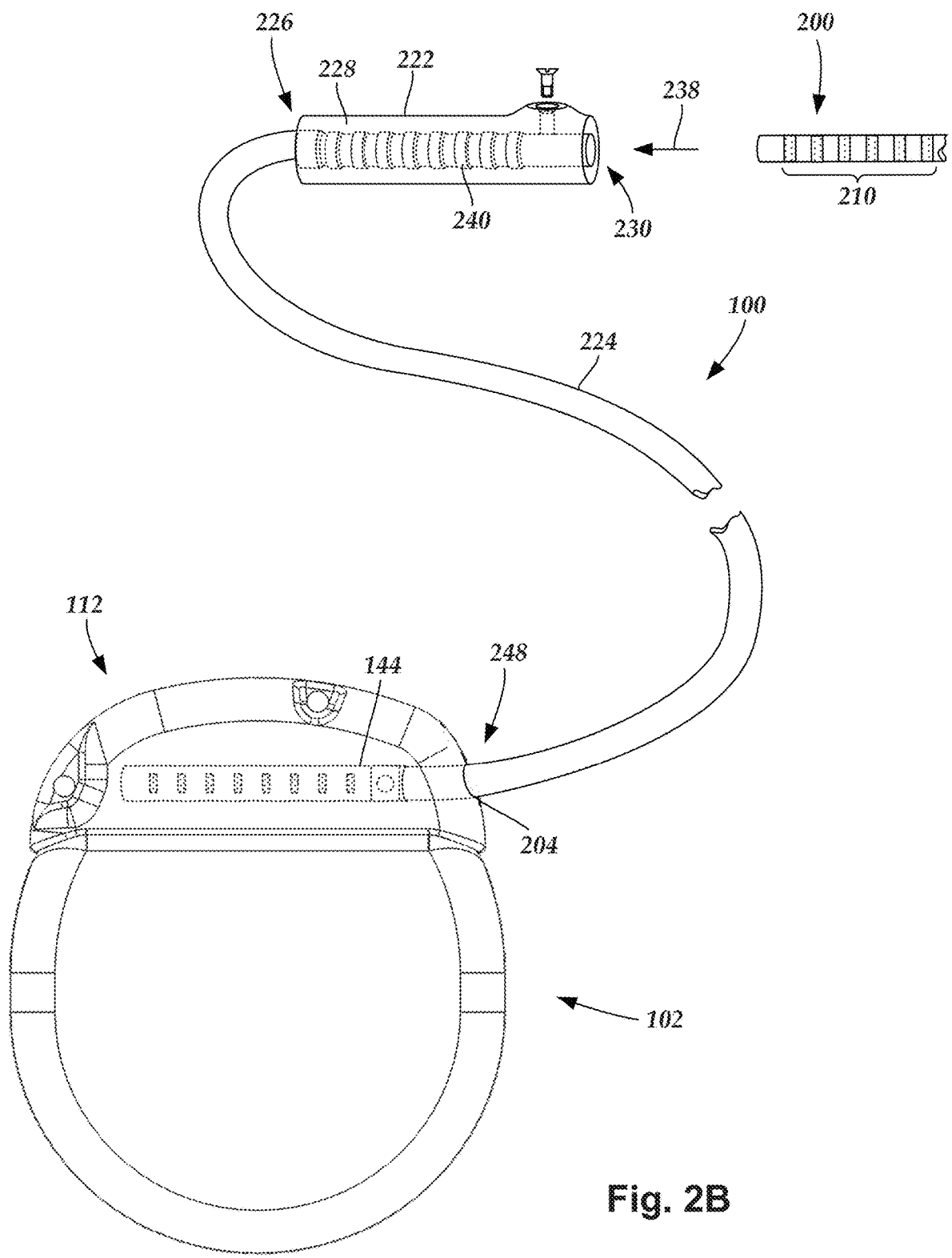
FIG. 2B is a schematic view of one embodiment of a proximal portion of a lead and a lead extension of an electrical stimulation system.

Terminals (e.g., 210 in FIGS. 2A-2B) are typically disposed along the proximal end of the one or more proximal portions of the electrical stimulation system 100 (as well as any splitters, lead extensions, adaptors, or the like) for electrical connection to corresponding connector contacts (e.g., 214 in FIG. 2A and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., a splitter, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

There can be challenges in delivering a lead to a desired lead implantation site. The lead implantation site can be, for example, the site in the body at which one or more of the electrodes of the lead are positioned when the lead is implanted. Alternatively, the lead implantation site can be the position of the distal tip (or other identified portion) of the lead.

One example of a challenging lead implantation site is the cervical spine. The easiest place to access the epidural space is down in the lumbar spine. Therefore, to place a lead in the cervical spine using epidural space access in the lumbar spine, a clinician must steer a lead many levels up the dorsal column, which is often difficult.

This disclosure presents new methods and associated components for implanting a lead. In at least some embodiments, the clinician can drive or otherwise deliver a lead blank into the epidural space at the lumbar or thoracic level and up to the desired lead implantation site in the cervical spine (or elsewhere). A long, flexible sheath can then be used to exchange the lead blank for a percutaneous electrical stimulation lead. The long, flexible sheath can also be used to exchange one lead for another to, for example, replace an old lead with a new one. The components described herein can be used for implantation or explanation of leads at locations other than the cervical spine. The components and methods disclosed herein can be used with other types of leads, such as optical leads.

FIGS. 3A and 3B illustrate one embodiment of a long, flexible sheath 350. The long, flexible sheath 350 has a body 352 (or cannula) and a hub 354. The hub 354 can facilitate grip, manipulation, and lead insertion and may be formed of any suitable material, such as, for example, polymers (for example, rigid polymers such as high-density polyethylene (HDPE), polypropylene, or the like) or metal or any combination thereof. The body 352 is flexible and thin. The body 352 can be made of any suitable material, such as, for example, polytetrafluoroethylene (PTFE), HDPE. or the like.

The sheath 350 defines a lumen into which a lead can be inserted and, therefore, has an inner diameter that is, for example, slightly larger than (or the same as) the outer diameter of the lead. In at least some embodiments, the distal tip 356 of the sheath 350 is tapered, as illustrated in FIGS. 3A and 3B, so that the inner diameter is narrower at the distal tip than at more proximal positions along the sheath to prevent or reduce tissue coring or inhibition of advancement by catching on tissue.

In at least some embodiments, the sheath 350 is suitable for implantation of a lead. In at least some embodiments, the sheath 350 is suitable for explanation of a lead with optional implantation of new lead. In at least some embodiments, the sheath 350 is sufficiently long to extend from the lumbar region to the cervical region of an average adult human male or female. In at least some embodiments, the long, flexible sheath 350 is at least 20, 25, 30, 35, 40, 45, or 50 cm long.

In at least some embodiments, the sheath 350 is splittable. A splittable hub 354 includes two (or more) pull-apart portions 351, 353. In some embodiments, the body 352 of the sheath 350 includes one or more perforated (or scored, weakened, thinned, or the like) regions extending along at least a portion of the longitudinal length of the sheath. In some embodiments, the body 352 is made of a material, such as PTFE, that reliably splits along the length of the sheath without perforation or scoring.

Figure 3C:
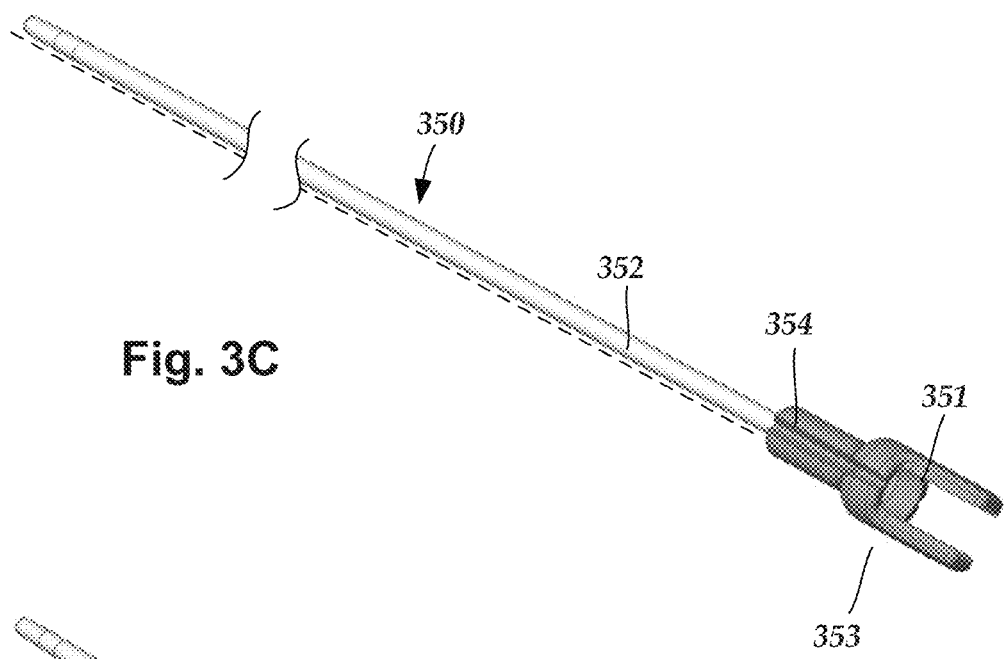
FIG. 3C is a schematic perspective view of the long, flexible sheath of FIG. 3A.
Figure 3D:
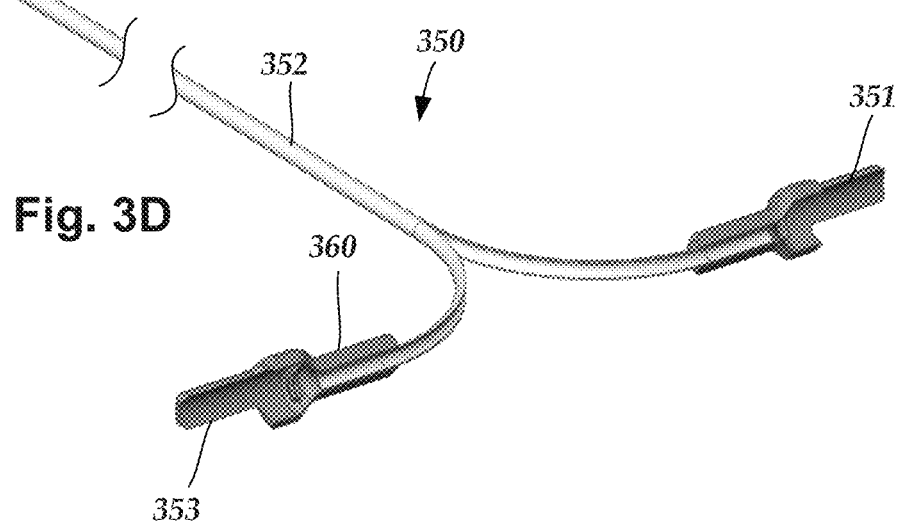
FIG. 3D is a schematic perspective view of the long, flexible sheath of FIG. 3A with the sheath partially split.

In at least some embodiments, the two pull-apart portions 351, 353 may also include one or more perforated (or scored, weakened, thinned, or the like) regions. In other embodiments, the two pull-apart portions 351, 353 may be spaced apart from each other with a gap between the two pull-apart portions. In at least some embodiments, when the two pull-apart portions 351, 353 are separated from one another, for example, by pulling each pull-apart portion laterally (for example, away from the other pull-apart portion in directions approximately orthogonal to the body 352 of the sheath 350), the body 352 of the sheath 350 separates, as illustrated in FIGS. 3C and 3D, and, if present, may separate along the one or more perforated (or scored, weakened, thinned, or the like) regions. In at least some embodiments, a splittable sheath 350 permits the insertion of non-isodiametric leads, with proximal features that will not fit through a closed canula.

FIGS. 4A and 4B illustrate one embodiment of a lead blank 370. A dedicated lead blank 370, designed for steering to a particular position rather than delivering electrostimulation therapy, can substantially ease placement of leads in difficult positions such as high cervical spine placement. In at least some embodiments, the lead blank 370 includes a lumen 372, which may extend from the proximal end to the distal end or no more than 75, 50, or 25% of the length of the led blank. The lead blank is open at the proximal end 372 can be either open or closed at the distal end 373. In other embodiments, the lead blank can be solid.

In at least some embodiments, the lead blank 370 can incorporate a larger lumen 372 (for receiving, for example, a stylet 374) than an electrical stimulation lead because the lead blank does not need to accommodate conductors and this may permit the use of thicker, stiffer stylets or stylets with special steering capabilities. In at least some embodiments, the lead blank 370 can have enhanced torque transfer compared to an electrical stimulation lead. In at least some embodiments, the lead blank 370 can be stiffer than is acceptable for an electrical stimulation lead that remains in the epidural space for a longer duration. A lead that is too stiff risks damaging the tissue in the spine by repeatedly pressing into tissue as the patient moves. A lead blank 370 that is only inserted into the epidural space for the duration of the procedure does not carry such a risk. Therefore, it can have a stiffer design, which can be advantageous for steering. Examples of stiffer materials for use with the lead blank include, but are not limited to, polyurethane (preferably, with a stiffness of at least 75 D), or the like. Other suitable materials include, but are not limited to, silicone, polyurethane, nylon, polyester, or the like. A lead blank 370 may have any combination of the features and advantages over an electrical stimulation lead described hereinabove.

In at least some embodiments, the lead blank 370 includes a stylet 374 disposed or insertable into a lumen 372 divided along the lead blank 370. In at least some embodiments, the stylet 374 is removable from the lead blank 370. In other embodiments, the stylet 374 is permanently disposed within the lead blank 370. The stylet 374 can be formed from any suitable material including, for example, nylon, polyester, polyurethane, other polymers, stainless steel, or the like. In at least some embodiments, the stylet 374 is sufficiently rigid to be insertable through the lumen 372 of the lead blank 370. In at least some embodiments, the stylet 374 includes a handle 376. Any suitable stylet 374 can be used.

The long, flexible sheath 350 and the lead blank 370 can be part of a kit for implanting a lead. The kit may also include one or more of the stylet 374, a needle 380 (FIG. 5A), or a lead, such as lead 103 of FIG. 1 or any other suitable lead. The long, flexible sheath 350 can be part of a kit for explanting a lead. The kit may also include one or more of the stylet 374, the lead blank 370, or a replacement lead, such as lead 103 of FIG. 1 or any other suitable lead.

Figure 5A:
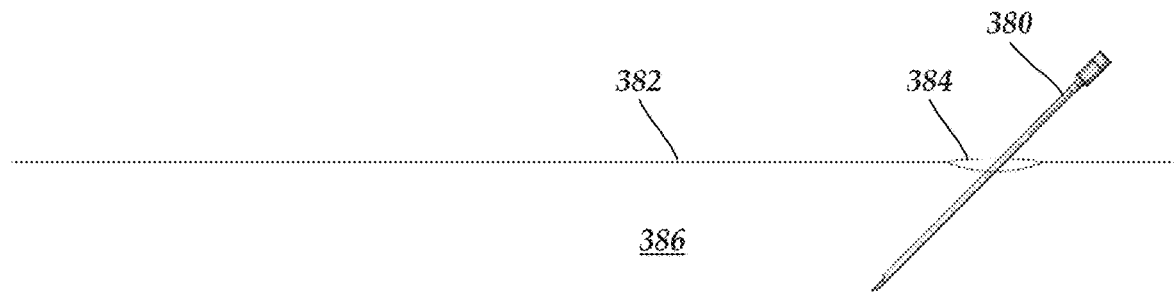
FIGS. 5A-5G are schematic side views of different steps in one embodiment of a method of implanting a lead using the long, flexible sheath of FIG. 3A and lead blank of FIG. 4A.

FIGS. 5A to 5G illustrate one embodiment of a method for implanting a lead 103 using the long, flexible sheath 350 and the lead blank 370. In FIGS. 5A to 5G and FIGS. 6A to 6E, the line 382 represents the skin of the patient with an opening 384 into the body of the patient. In FIG. 5A, a needle 380 is inserted through the skin 382 of the patient into the epidural space 386. The needle 380 includes a hub 388 and lumen 390 through the needle. In at least some embodiments, the needle 380 extends into the epidural space 386, but does not extend to the desired implantation site. For example, the needle 380 may be inserted into at the epidural space at a lumbar or thoracic vertebral level with the desired implantation site elsewhere along the spinal column, such as at a cervical vertebral level.

Figure 5B:
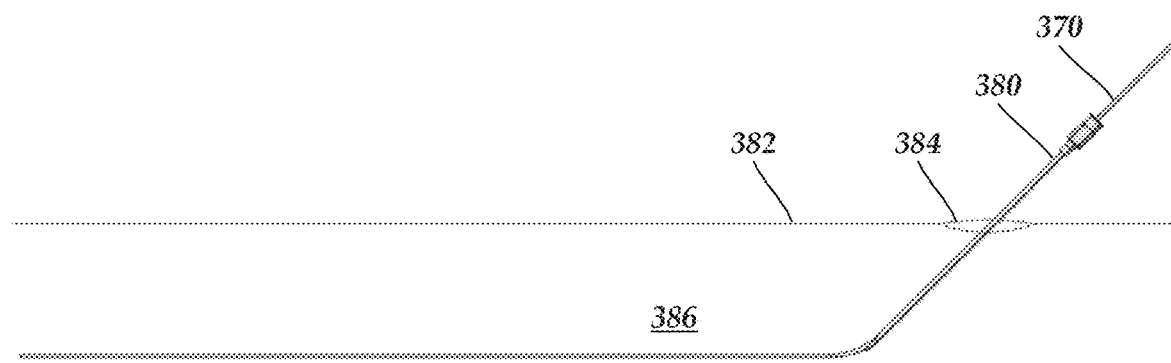

As illustrated in FIG. 5B, the lead blank 370 is inserted into the lumen 390 of the needle 380 and enters the epidural space 386. The lead blank 370 is steered to, or near, the desired implantation site. In at least some embodiments, as illustrated in FIG. 5B, much (or even most—for example, at least 50, 60, 70, or 80%) of the lead blank 370 exits the distal end 392 of the needle 380 as it is inserted and steered. In at least some embodiments, the length of the needle is no more than 50%, 40%, 33%, 30%, or 20% of the length of the lead blank. As described above, in at least some embodiments, the lead blank 370 includes a stylet 374 that is used to steer the lead blank.

Figure 5C:
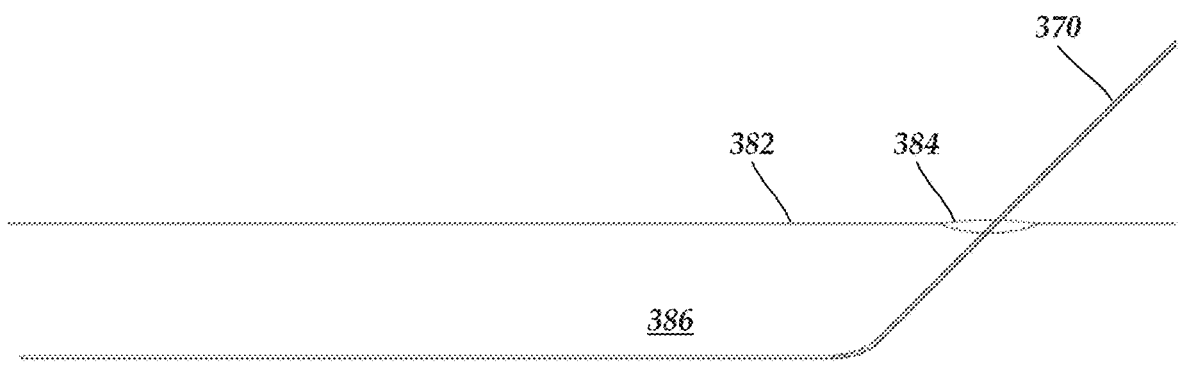
Figure 5D:
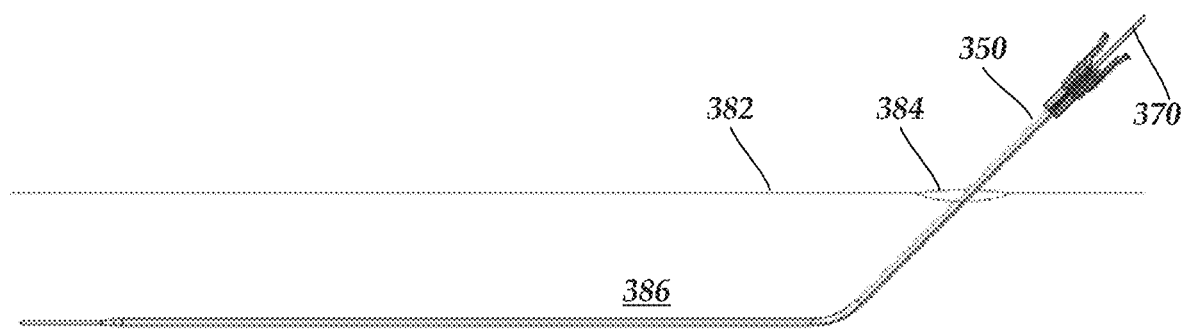

When the lead blank 370 is inserted (and optionally at, or near, the desired implantation site) the needle 380 is removed, as illustrated in FIG. 5C. After removal of the needle 380, the long, flexible sheath 350 is inserted over the lead blank 370, as illustrated in FIG. 5D. In at least some embodiments, the long, flexible sheath 350 is inserted, and advanced, over the lead blank 370 after the lead blank has been placed at, or near the desired implantation site. In other embodiments, the long, flexible sheath 350 is inserted, and advanced, over the lead blank 370 prior to the lead blank being placed at, or near the desired implantation site and the combination of the sheath 350 and lead blank 370 is further steered toward the desired implantation site.

In at least some embodiments, the handle 376 of the stylet 374 (or another handle associated with the lead blank 370) is used to hold the lead blank in place as the long, flexible sheath 350 is inserted over the lead blank. Preferably, the combined length of the handle then the portion of the lead blank outside the patient's body is at least as long as the sheath. In other embodiments, a suture may be attached to the lead blank 370 to act as a "leash" to hold the lead blank in place as the sheath 350 is advanced over the lead. Preferably, the suture is at least as long as the sheath 350. In at least some embodiments, the handle or suture is inserted through the sheath 350 prior to insertion of the sheath over the lead blank 370.

Figure 5E:
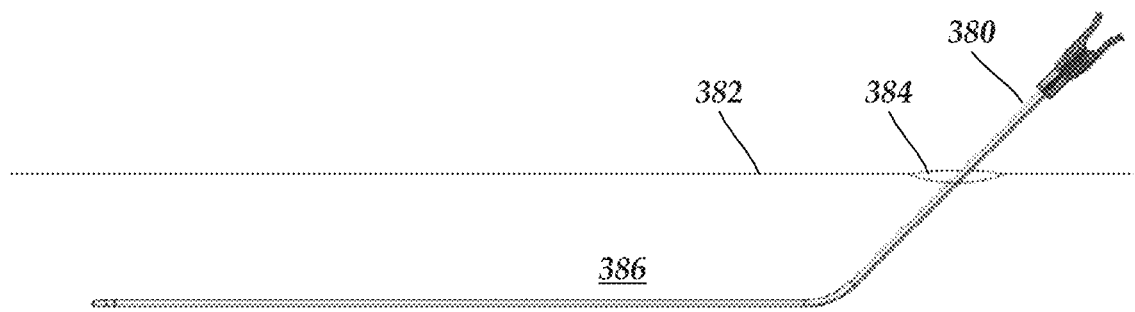
Figure 5F:
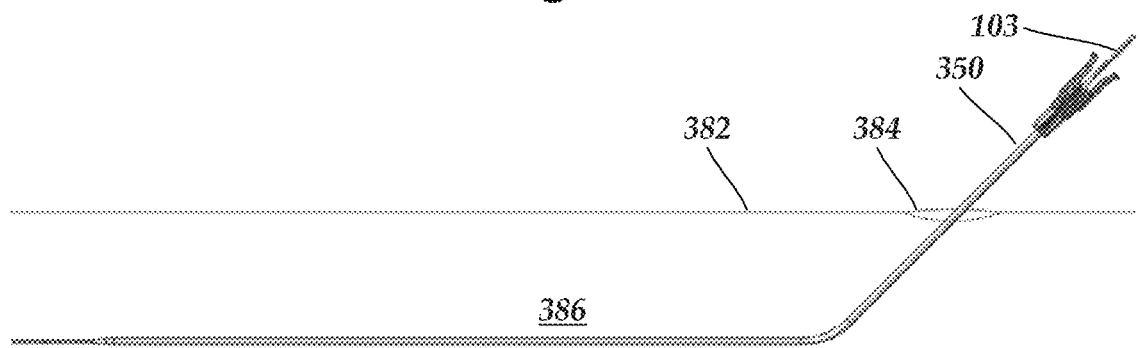
Figure 5G:
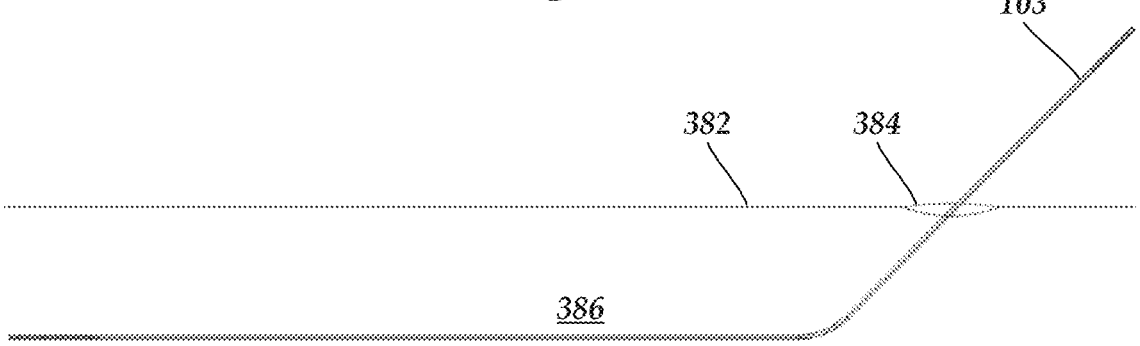

When the long, flexible sheath 350 is positioned at, or near, the desired implantation site, the lead blank 370 is removed, as illustrated in FIG. 5E. A lead 103 is then inserted into the long, flexible sheath 350 and pushed to the desired implantation site, as illustrated in FIG. 5F. When the lead 103 is in place, the long, flexible sheath 350 is removed, leaving the lead 103, as illustrated in FIG. 5G. In at least some embodiments, the long, flexible sheath 350 is splittable (see, FIGS. 3C and 3D) and can be removed by splitting the sheath into at least two parts. In other embodiments, the sheath 350 may be pulled back, leaving the lead 103 in place.

Figure 6A:
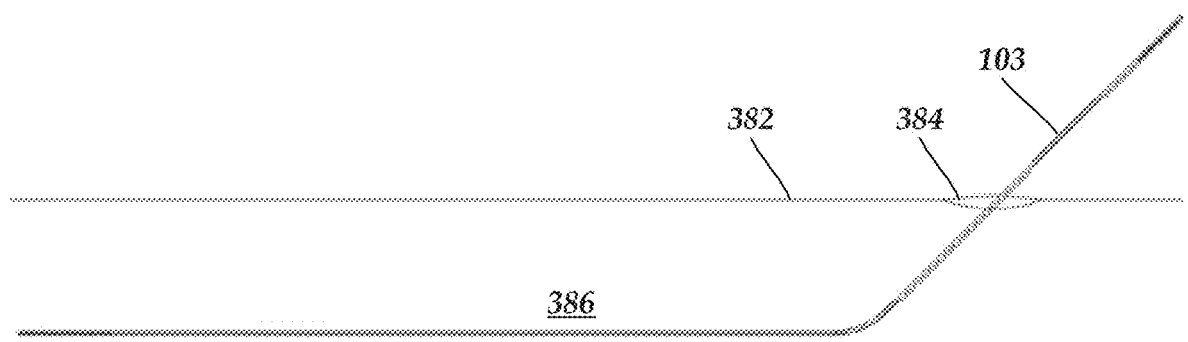
FIGS. 6A-6E are schematic side views of different steps in one embodiment of a method of explanting a lead and implanting a new lead using the long, flexible sheath of FIG. 3A.
Figure 6B:
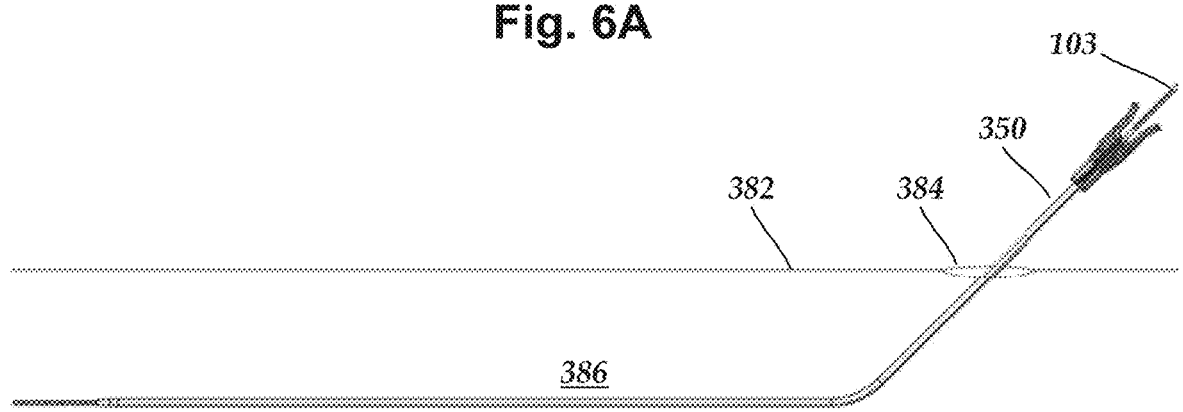

FIGS. 6A to 6E illustrate one embodiment of a method of explanting a lead and replacing the lead with a new lead. FIG. 6A illustrates an implanted lead 103. In FIG. 6B, a long, flexible sheath 350 is inserted through the opening 384 in the skin of the patient and advanced over the lead 103.

Figure 6C:
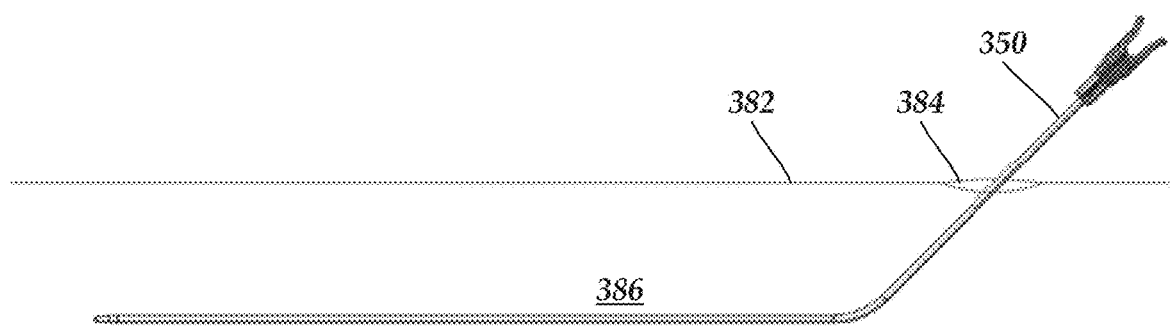

Once the sheath 350 is in place over the lead 103, the lead can be removed, as illustrated in FIG. 6C.

Figure 6D:
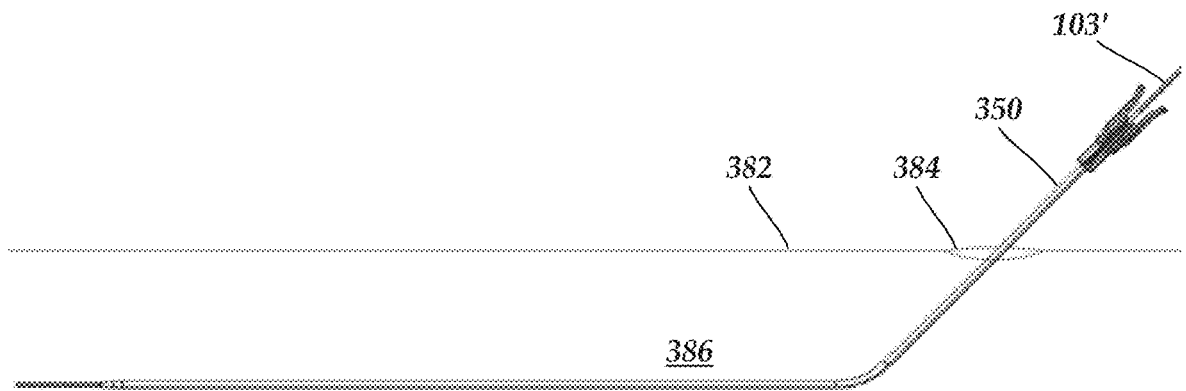

The new lead 103' is then inserted through the sheath 350, as illustrated in FIG. 6D, and positioned at the desired implantation site. In some embodiments, the implantation site for the new lead 103' is the same as the implantation site for the original lead 103. In some instances, however, the lead 103 may have migrated from the original implantation site or the clinician may desire to implant the new lead 103' at a different implantation site. In some embodiments, the new lead 103' may be steered to a new position. In some other embodiments, a lead blank 370 (FIGS. 4A and 4B) may be inserted into the sheath 350 prior to the new lead 103' and steered to the new implantation site. The lead blank 370 is then removed and the new lead 103' inserted, as illustrated in FIG. 6D.

Figure 6E:
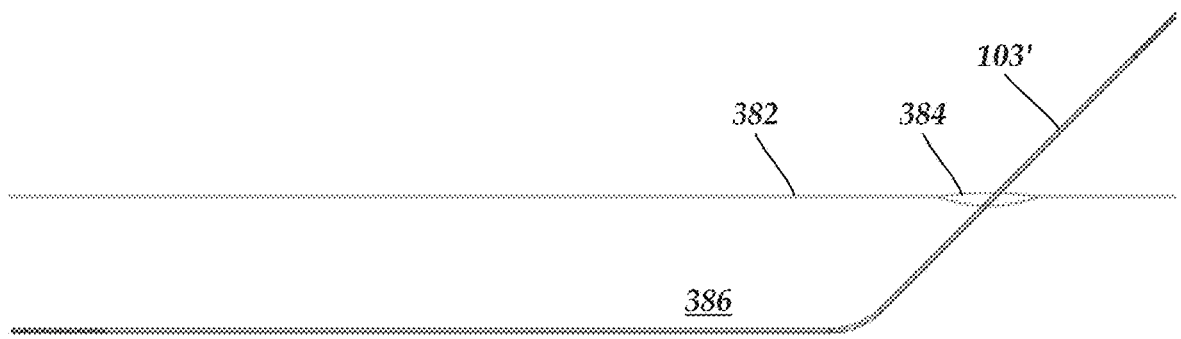

When the new lead 103' is in place, the long, flexible sheath 350 is removed, leaving the new lead 103', as illustrated in FIG. 6E. In at least some embodiments, the long, flexible sheath 350 is splittable (see, FIGS. 3C and 3D) and can be removed by splitting the sheath into at least two parts. In other embodiments, the sheath 350 may be pulled back, leaving the new lead 103' in place.

The methods illustrated in FIGS. 5A to 5G and 6A to 6E are directed to implanting or explanting a lead for spinal cord stimulation. It will be understood that the long, flexible sheath 350 and lead blank 370 and other components described herein can be used for implanting or explanting leads in other portions of the body of the patient.

Figure 7:
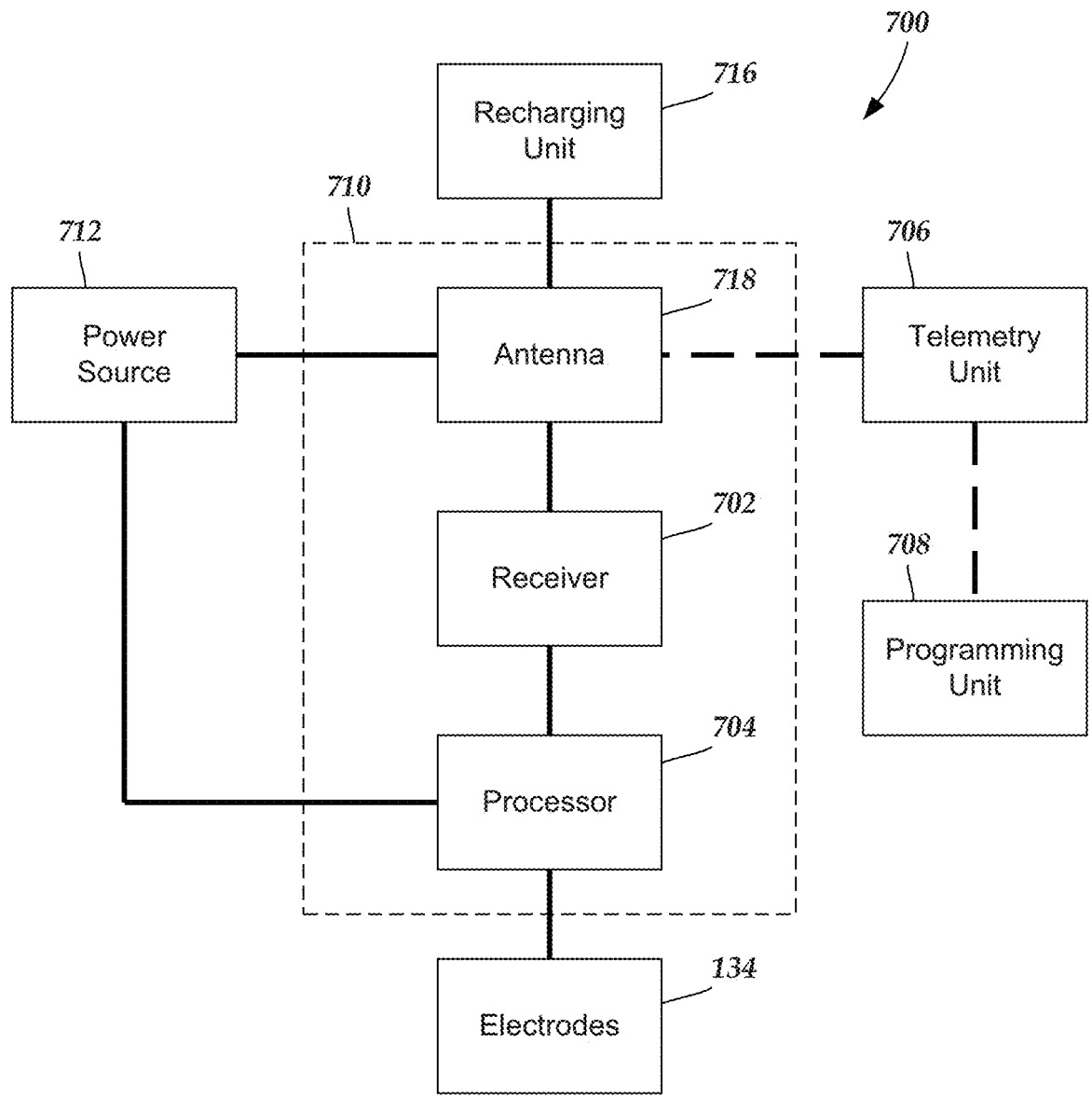
FIG. 7 is a schematic overview of one embodiment of components of a stimulation system, including an electronic subassembly disposed within a control module.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 74 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the invention and the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A method for implanting a lead in a patient, the method comprising:
   inserting a needle into the patient;
   inserting a lead blank through the needle;
   steering the lead blank to, or near, a lead implantation site;
   removing the needle from the patient and leaving the lead blank;
   advancing a flexible sheath over the lead blank after removing the needle;
   removing the lead blank from the patient and leaving the flexible sheath;
   inserting a lead through the flexible sheath, after removing the lead blank, and implanting the lead at the lead implantation site; and
   removing the flexible sheath.

2. The method of claim 1, wherein inserting the needle into the patient comprises inserting the needle into an epidural space of the patient at a lumbar or thoracic vertebral level.

3. The method of claim 2, wherein the lead implantation site is at a cervical vertebral level.

4. The method of claim 1, wherein the flexible sheath has a length of at least 30 CM.

5. The method of claim 1, wherein the needle has a length that is no more than 40% of a length of the lead blank.

6. The method of claim 1, wherein the steering of the lead blank occurs prior to removal of the needle.

7. The method of claim 1, wherein the flexible sheath comprises a flexible body and a rigid hub coupled to the flexible body and comprising two pull-apart tabs, wherein removing the flexible sheath comprises pulling apart the two pull-apart tabs and splitting the flexible body of the flexible sheath.

8. The method of claim 1, wherein steering the lead blank occurs prior to advancing the flexible sheath over the lead blank.

9. The method of claim 1, wherein the flexible sheath has a tapered distal end to reduce an inner diameter of the flexible sheath.

10. The method of claim 1, wherein the lead blank defines a lumen and further comprises a stylet configured to be disposed in the lumen.

11. The method of claim 1, wherein the lead blank comprises a handle or suture attached to the lead blank to hold the lead blank in place when the flexible sheath is advanced over the lead blank.

12. The method of claim 1, wherein the flexible sheath comprises a flexible body having a proximal end and a distal end, the flexible body defining a lumen, and a rigid hub coupled to the proximal end of the flexible body and defining an opening to the lumen of the flexible body.

13. The method of claim 1, wherein the lead blank has a length at least as long as a length of the flexible sheath.

14. The method of claim 1, wherein inserting the lead blank through the needle comprises inserting the lead bank into a lumen of the needle so that a portion of the lead blank exits a distal end of the needle.

15. The method of claim 1, wherein advancing the flexible sheath over the lead blank occurs after steering the lead blank to, or near, the lead implantation site.

16. The method of claim 1, wherein advancing the flexible sheath over the lead blank occurs prior steering the lead blank to, or near, the lead implantation site.

17. The method of claim 1, wherein the flexible sheath is splittable and removing the flexible sheath comprises splitting the flexible sheath into at least two parts.

18. The method of claim 1, wherein removing the flexible sheath comprises pulling back the flexible sheath leaving the lead in place.

19. The method of claim 10, wherein the lumen extends from a proximal end of the lead blank to a distal end of the lead blank.

20. The method of claim 10, wherein the lumen extends no more than 75% of a length of the lead blank.

* * * * *